(12) United States Patent
Kath et al.

(10) Patent No.: US 6,465,449 B1
(45) Date of Patent: Oct. 15, 2002

(54) HETEROAROMATIC BICYCLIC DERIVATIVES USEFUL AS ANTICANCER AGENTS

(75) Inventors: John Charles Kath; Norma Jacqueline Tom, both of Waterford; Eric David Cox, Mystic; Samit Kumar Bhattacharya, Groton, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/488,378

(22) Filed: Jan. 20, 2000

Related U.S. Application Data

(60) Provisional application No. 60/117,341, filed on Jan. 27, 1999.

(51) Int. Cl.$^7$ ............... A61K 31/33; A61K 31/517; C07D 239/72
(52) U.S. Cl. ............... 514/183; 514/266.1; 514/266.2; 544/293; 544/284
(58) Field of Search ............... 544/293, 284; 514/183, 266.1, 266.2

(56) References Cited

U.S. PATENT DOCUMENTS

| | | | |
|---|---|---|---|
| 5,256,781 A | 10/1993 | Primeau et al. | 544/293 |
| 5,283,242 A | 2/1994 | Ellingboe | 514/186 |
| 5,360,809 A | 11/1994 | Axelsson | 514/338 |
| 5,736,534 A | 4/1998 | Arnold | 514/63 |
| 5,747,498 A | 5/1998 | Schnur et al. | 514/259 |
| 5,866,572 A | 2/1999 | Barker et al. | 514/234.5 |

FOREIGN PATENT DOCUMENTS

| | | |
|---|---|---|
| CA | 2225366 | 6/1998 |
| EP | 0414386 | 2/1991 |
| EP | 0520722 | 12/1992 |
| EP | 0566226 | 10/1993 |
| EP | 0602851 | 6/1994 |
| EP | 0635498 | 1/1995 |
| EP | 0635507 | 1/1995 |
| EP | 0837063 | 4/1998 |
| EP | 0882717 | 12/1998 |
| WO | 9220642 | 11/1992 |
| WO | WO 9307146 | 4/1993 |
| WO | WO 9515758 | 6/1995 |
| WO | WO 9519774 | 7/1995 |
| WO | WO 9523141 | 8/1995 |
| WO | 9523141 * | 8/1995 |
| WO | 9609294 | 3/1996 |
| WO | 9616960 | 6/1996 |
| WO | WO 9628430 | 9/1996 |
| WO | WO 9630347 | 10/1996 |
| WO | WO 9640142 | 12/1996 |
| WO | 9721701 | 6/1997 |
| WO | WO 9722596 | 6/1997 |
| WO | 9730034 * | 8/1997 |
| WO | WO 9730044 | 8/1997 |
| WO | 9802434 | 1/1998 |
| WO | 9802437 | 1/1998 |
| WO | 9802438 | 1/1998 |

OTHER PUBLICATIONS

Spada et al., "Small Molecule Inhibitors of Tyrosine Kinase Activity," Expert Opinion to Therapeutic Patents, GB, Ashley Publications, vol. 5, No. 8, Jan. 1, 1995.

Craciunescu et al., "Study of the "in vivo" Dueal (Antitumor and Trypanocidal) Pharmacological Effects Displayed By Dimeric and Neutral New Complexes of Iridium (II) and Rhodium (II) With Classical Antimalarial Drugs," An. R. Acad. Farm., 1991, 57(1), 15–35. CAPLUS 1992:33922 only.

Nomoto et al., "Studies on Cardiotonic Agents. VI. Potent Cardiotonic Agent KF15232 With Myofribillar Calcium Sensitizing Effect," Chem. Pharm. Bull., 1991, 39(4), 900–910. CAPLUS 1991:505945 only.

* cited by examiner

Primary Examiner—Mukund J. Shah
Assistant Examiner—Sudhaker B. Patel
(74) Attorney, Agent, or Firm—Peter C. Richardson; Paul H. Ginsburg; Adrian G. Looney

(57) ABSTRACT

The invention relates to compounds of the formula 1

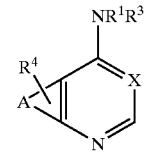

and to pharmaceutically acceptable salts and solvates thereof, wherein A, X, $R^1$, $R^3$ and $R^4$ are as defined herein. The invention also relates to methods of treating abnormal cell growth in mammals by administering the compounds of formula 1 and to pharmaceutical compositions for treating such disorders which contain the compounds of formula 1. The invention also relates to methods of preparing the compounds of formula 1.

8 Claims, No Drawings

HETEROAROMATIC BICYCLIC DERIVATIVES USEFUL AS ANTICANCER AGENTS

This application claims the benefit of U.S. Provisional Application No. 60/117,341 filed Jan. 27, 1999, which is incorporated herein by reference.

BACKGROUND OF THE INVENTION

This invention relates to novel bicyclic derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, VEGF and TGF-β. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor. Thus, the compounds of the present invention, which are selective inhibitors of certain receptor tyrosine kinases, are useful in the treatment of abnormal cell growth, in particular cancer, in mammals.

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97130034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose.

SUMMARY OF THE INVENTION

The present invention relates to compounds of the formula 1

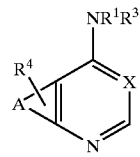

and to pharmaceutically acceptable salts and solvates thereof, wherein: X is N or CH;

A represents a fused 5, 6 or 7-membered ring optionally containing 1 to 4 heteroatoms which may be the same or different and which are selected from —N($R^1$)—, O, and S(O)$_j$, wherein j is an integer from 0 to 2, the fused ring containing a total of 1, 2 or 3 double bonds inclusive of the bond in the pyridine or pyrimidine ring to which it is fused wherein the $R^1$ group attached to the nitrogen is absent if a double bond includes the foregoing optional nitrogen moiety —N($R^1$)—, with the proviso that the fused ring does not form part of a purine and that the fused ring does not contain two adjacent O or S(O)$_j$ atoms, and wherein the carbon atoms of the A moiety are optionally substituted with 1 to 3 $R^5$ groups;

each $R^1$ and $R^2$ is independently H or $C_1$–$C_6$ alkyl;
$R^3$ is —($CR^1R^2$)$_m$-$R^8$ wherein m is 0 or 1;
or $R^1$ and $R^3$ are taken together to form a group of the formula

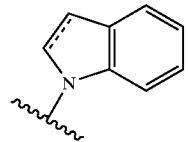

wherein said group is optionally substituted with 1 to 3 $R^5$ groups;

$R^4$ is —($CR^1R^2$)$_t$($C_6$–$C_{10}$ aryl) or —($CR^1R^2$)$_t$(4–10 membered heterocyclic), wherein t is an integer from 0 to 5, wherein said $R^4$ groups are substituted with 1 to 3 groups independently selected from —($CR^1R^2$)$_q$$NR^1R^9$, —($CR^1R^2$)$_q$$NR^9$($C_1$–$C_6$ alkanoyl), —($CR^1R^2$)$_q$O($CR^1R^2$)$_r$$R^9$, and —($CR^1R^2$)$_q$$R^9$ wherein q and r are each independently an integer from 0 to 5, and wherein the heterocyclic, aryl and alkyl moieties of the foregoing groups are optionally substituted with 1 to 3 $R^{10}$ groups;

each $R^5$ is independently selected from halo, hydroxy, —$NR^1R^2$, $C_1$–$C_6$ alkyl, trifluoromethyl, $C_1$–$C_6$ alkoxy, and trifluoromethoxy;

each $R^6$ and $R^7$ is independently selected from H, $C_1$–$C_6$ alkyl, —($CR^1R^2$)$_t$($C_6$–$C_{10}$ aryl), and —($CR^1R^2$)$_t$(4–10 membered heterocyclic), wherein t is an integer from 0 to 5, 1 or 2 ring carbon atoms of the heterocyclic group are optionally substituted with an oxo (═O) moiety, and the alkyl, aryl and heterocyclic moieties of the foregoing $R^6$ and $R^7$ groups are optionally substituted with 1 to 3 substituents independently selected from halo, cyano, nitro, —$NR^1R^2$, trifluoromethyl, trifluoromethoxy, $C_1$–$C_6$ alkyl, $C_2$–$C_6$ alkenyl, $C_2$–$C_6$ alkynyl, hydroxy, and $C_1$–$C_6$ alkoxy;

each $R^8$ is independently selected from —$(CR^1R^2)_t$, ($C_6$–$C_{10}$ aryl) and —$(CR^1R^2)_t$(4–10 membered heterocyclic), wherein t is an integer from 0 to 5, 1 or 2 ring carbon atoms of the heterocyclic group are optionally substituted with an oxo (=O) moiety, and each of the foregoing $R^8$ groups is optionally substituted with 1 to 5 $R^{10}$ groups;

$R^9$ is a fused or bridged bicyclic ring or a spirocyclic ring, wherein said ring contains from 5 to 12 carbon atoms in which up to 2 carbon atoms are optionally replaced with a hetero moiety selected from O, $S(O)_j$ wherein j is an integer from 0 to 2, and —$NR^{11}$—, provided that two O atoms, two $S(O)_j$ moieties, an O atom and a $S(O)_j$ moiety, an N atom and an S atom, or an N atom and an O atom are not attached directly to each other, and wherein said ring is saturated or partially unsaturated with up to two carbon-carbon double bonds, and the carbon atoms of said ring are optionally substituted with 1 to 4 $R^{10}$ groups;

or where $R^9$ is as —$NR^1R^9$ then $R^9$ optionally can be taken together with $R^1$ and the nitrogen to which $R^1$ and $R^9$ are attached to form a fused or bridged bicyclic ring or a spirocyclic ring, wherein said ring is saturated and contains from 5 to 12 carbon atoms in which up to 2 carbon atoms are optionally replaced with a hetero moiety selected from O, $S(O)_j$ wherein j is an integer from 0 to 2, and —$NR^1$—, provided that two O atoms, two $S(O)_j$ moieties, or an O atom and a $S(O)_j$ moiety are not attached directly to each other, and wherein the carbon atoms of said rings are optionally substituted with 1 to 4 $R^{10}$ groups;

each $R^{10}$ is independently selected from halo, cyano, nitro, trifluoromethoxy, trifluoromethyl, azido, hydroxy, $C_1$–$C_6$ alkoxy, $C_1$–$C_{10}$ alkyl, $C_2$–$C_6$ alkenyl, $C_2$–$C_6$ alkynyl, —$C(O)R^5$, —$C(O)OR^6$, —$OC(O)R^6$, —$NR^8C(O)R^7$, —$C(O)NR^6R^7$, —$NR^6R^7$, —$NR^6OR^7$, —$SO_2NR^6R^7$, —$S(O)_j(C_1$–$C_6$ alkyl) wherein j is an integer from 0 to 2, —$(CR^1R^2)_t(C_6$–$C_{10}$ aryl), —$(CR^1R^2)_t$(4–10 membered heterocyclic), —$(CR^1R^2)_qC(O)(CR^1R^2)_t(C_6$–$C_{10}$ aryl), —$(CR^1R^2)_qC(O)(CR^1R^2)_t$(4–10 membered heterocyclic), —$(CR^1R^2)_tO(CR^1R^2)_q(C_6$–$C_{10}$ aryl), —$(CR^1R^2)_tO(CR^1R^2)_q$(4–10 membered heterocyclic), —$(CR^1R^2)_qSO_2(CR^1R^2)_t(C_6$–$C_{10}$ aryl), and —$(CR^1R^2)_qSO_2(CR^1R^2)_t$(4–10 membered heterocyclic), wherein q and t are each independently an integer from 0 to 5, 1 or 2 ring carbon atoms of the heterocyclic moieties of the foregoing $R^{10}$ groups are optionally substituted with an oxo (=O) moiety, and the alkyl, alkenyl, alkynyl, aryl and heterocyclic moieties of the foregoing $R^{10}$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^1$, —$C(O)NR^6R^7$, —$NR^6R^7$, —$NR^6OR^7$, $C_1$–$C_6$ alkyl, $C_2$–$C_6$ alkenyl $C_2$–$c_6$ alkynyl —$(CR^1R^2)_t(C_6$–$C_{10}$ aryl), and —$(CR^1R^2)_t$(4–10 membered heterocyclic), wherein t is an integer from 0 to 5;

$R^{11}$ is H, $C_1$–$C_6$ alkyl, —$C(O)R^6$ or —$SO_2R^6$;

and wherein any of the above-mentioned substituents comprising a $CH_3$ (methyl), $CH_2$ (methylene), or CH (methine) group which is not attached to a halogeno, SO or $SO_2$ group or to a N, O or S atom optionally bears on said group a substituent selected from hydroxy, halo, $C_1$–$C_4$ alkyl, $C_1$–$C_4$ alkoxy and —$NR^1R^2$.

In a specific embodiment of the present invention, the A moiety of the compounds of formula 1 is selected from

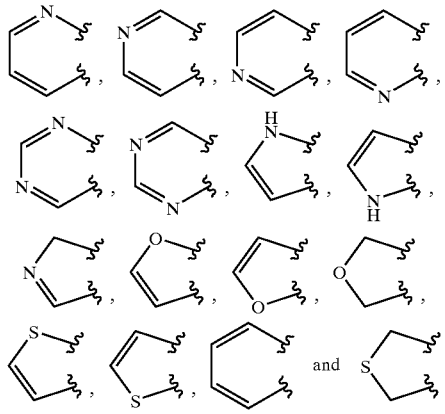

wherein the above A moieties bear an $R^4$ group as a substituent and optionally bear 1 to 3 $R^5$ groups as substituents.

Other specific embodiments of the compounds of formula 1 include those wherein A is elected from

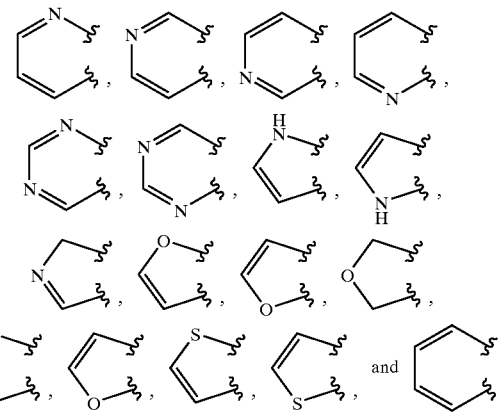

wherein the above A moieties bear an $R^4$ group as a substituent and optionally bear 1 to 3 $R^5$ groups as substituents.

Other specific embodiments of the compounds of formula 1 include those wherein A is selected from

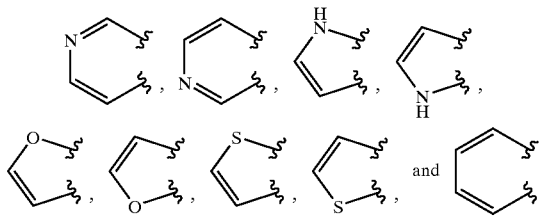

wherein the above A moieties bear an $R^4$ group as a substituent and optionally bear 1 to 3 $R^5$ groups as substituents.

Other specific embodiments of the compounds of formula 1 include those wherein A is selected from

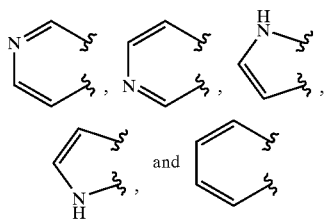

wherein the above A moieties bear an $R^4$ group as a substituent and optionally bear 1 to 3 $R^5$ groups as substituents.

Other specific embodiments of the compounds of formula 1 include those wherein A is

wherein the above A moieties bear an $R^4$ group as a substituent and optionally bear 1 to 3 $R^5$ groups as substituents.

Other specific embodiments of the compounds of formula 1 include those wherein $R^4$ is $-(CR^1R^2)_t(C_6-C_{10}$ aryl) or $-(CR^1R^2)_t$(4–10 membered heterocyclic), wherein t is an integer from 0 to 5, wherein said $R^4$ groups are substituted with 1 to 3 groups independently selected from $-(CR^1R^2)_qNR^1R^9$, $-(CR^1R^2)_qNR^9(C_1-C_6$ alkanoyl), $-(CR^1R^2)_qO(CR^1R^2)_rR^9$, and $-(CR^1R^2)_qR^9$ wherein q and r are each independently an integer from 0 to 3, and wherein the heterocyclic, aryl and alkyl moieties of the foregoing groups are optionally substituted with 1 to 3 $R^{10}$ groups.

Other specific embodiments of the compounds of formula 1 include those wherein $R^3$ is $-(CR^1R^2)_mR^8$ wherein m is 0 or 1 and $R^8$ is selected from $-(CR^1R^2)_t$(phenyl), $-(CR^1R^2)_t$(pyridyl), $-(CR^1R^2)_t$(pyrimidinyl), $-(CR^1R^2)_t$(indolyl), $-(CR^1R^2)_t$(indazolyl) and $-(CR^1R^2)_t$(benzimidazolyl), wherein t is an integer from 0 to 5, and each of the foregoing $R^8$ groups is optionally substituted with 1 to 5 $R^{10}$ groups.

Other specific embodiments of the compounds of formula 1 include those selected from the group consisting of:

{[4-(6-[4-(6-Amino-3-aza-bicyclo[3.1.0]hex-3-ylmethyl)-phenyl]quinazolin-4-yl}-(4-phenoxy-phenyl)-amine;

(3-{4-[4-(4-Benzyl-phenylamino)quinazolin6-yl]-benzy}-3-aza-bicyclo[3.1.0]hex-6-yl)-methanol;

(3-{4-[4-(4-Phenoxy-phenylamino)-quinazolin-6-yl]-benzyl}-3-aza-bicyclo[3.1.0]hex-6-yl)-methanol;

(3-{4-[4-(1-Benzenesulfonyl-1H-indol-5-ylamino)-quinazolin6-yl]-benzyl}-3-aza-bicyclo[3.1.0]hex-6-yl)-methanol;

(6-{4-[(1-Aza-bicyclo[2.2.2]oct-3-ylamino)-methyl]-phenyl}-quinazolin-4-yl)-(4-phenoxy-phenyl)-amine;

(6-{4-[(1-Aza-bicyclo[2.2.2]-3-ylamino)-methyl]-phenyl}-quinazolin-4-yl)-(4-benzyl-phenyl)-amine;

6-{4-[(1-Aza-bicyclo[2.2.2]oct-3-ylamino)-methyl]-phenyl}-quinazolin-4-yl)-(1-benzenesulfonyl-1H-indol-5-yl)-amine;

6-{4-[(3-Aza-bicyclo[3.1.0]hex-6-ylamino)-methyl]-phenyl}-quinazolin-4-yl)-(4-phenoxy-phenyl)-amine;

3-{4-[4-(4-Benzyl-phenylamino)-quinazolin6-yl]-benzylamino}-8-methyl-8-aza-bicyclo[3.2.1]octan6-ol;

(4-Benzyl-phenyl)-{6-[4-(6-methoxymethyl-3-aza-bicyclo[3.1.0]hex-3-ylmethyl)-phenyl]-quinazolin-4-yl}-amine {6-[4-(6-Methoxymethyl-3-aza-bicyclo[3.1.0]hex-3-ylmethyl)-phenyl]-quinazolin4-yl}-(4-phenoxy-phenyl)-amine;

(3-{4-[4-(4-[1,2,3]Thiadiazol-5-yl-phenylamino)-quinazolin-6-yl]-benzyl}-3-aza-bicyclo[3.1.0]hex-6-yl)-methanol;

(3-{4-[4-(4-Cyclohexyl-phenylamino)-quinazolin-6-yl]-benzyl}-3-aza-bicyclo[3.1.0]hex6-yl)-methanol;

(3-{4-[4-(4-p-Tolyloxy-phenylamino)-quinazolin-6-yl]-benzyl}-3-aza-bicyclo[3.1.0]hex6-yl)-methanol;

(3-{4-[4-(Biphenyl4-ylamino)-quinazolin-6-yl]-benzyl}-3-aza-bicyclo[3.1.0]hex-6-yl)-methanol;

(3-{4-[4-(4-Ethyl-phenylamino)-quinazolin-6-yl]-benzyl}-3-aza-bicyclo[3.1.0]hex-6-yl)-methanol;

4-{6-[4-(6-Hydroxymethyl-3-aza-bicyclo[3.1.0]hex-3-ylmethyl)-phenyl]-quinazolin-4-ylamino}-N-phenyl-benzamide;

[3-(4-{4-[1-(Propane-2-sulfonyl)-1H-indol-5-ylamino]-quinazolin6-yl}-benzyl)-3-aza-bicyclo[3.1.0]hex-6-yl]-methanol;

(3-{4-[4-(1-Benzyl-1H-indazol-5-ylamino)-quinazolin-6-yl]-benzyl}-3-aza-bicyclo[3.1.0]hex-6-yl)-methanol;

(1-Benzenesulfonyl-1H-indol-5-yl)-(6-{4-[(3-oxa-bicyclo[3.1.0]hex-6-ylamino)-methyl]-phenyl)-quinazolin-4-yl)-amine;

8-{4-[4-(1-Benzenesulfonyl-1H-indol-5-ylamino)-quinazolin-6-yl]-benzyl}-8-aza-bicyclo[3.2.1]octan-3-ol;

8-(4-{4-[1-(Propane-2-sulfonyl)-1H-indol-5-ylamino]-quinazolin-6-yl}-benzyl)-8-aza-bicyclo[3.2.1]octan-3-ol;

8-{4-[4-(4-Phenoxy-phenylamino)-quinazolin-6-yl]-benzyl}-8-aza-bicyclo[3.2.1]octan-3-ol;

8-{4-[4-(1-Benzyl-1H-indol-5-ylamino)-quinazolin-6-yl]-benzyl}-8-aza-bicyclo[3.2.1]octan-3-ol;

(3-{4-[4-(6-Phenoxy-pyridin-3-ylamino)-quinazolin-6-yl]-benzyl}-3-aza-bicyclo[3.1.0]hex-6-yl)-methanol;

(3-{5-[4-(4-Benzyl-phenylamino)-quinazolin-6-yl]-pyrdin-2-ylmethyl}3-aza-bicyclo[3.1.0]hex-6-yl)-methanol;

{3-[4-(4-Phenoxy-phenylamino)-quinazolin-6ylmethyl]-3-aza-bicyclo[3.1.0]hex-6-yl}methanol;

5-{4-[4-(1-Benzenesulfonyl-1H-indol-5-ylamino)-quinazolin-6-yl]-benzyl}-5-aza-spiro[2.5]oct-1-yl)-methanol;

(5-{4-[4-(4-Phenoxy-phenylamino)-quinazolin-6-yl]-benzyl}-5-aza-spiro[2.5]oct-1-yl)-methanol;

(6-{4-[4-(1-Benzenesulfonyl-1H-indol-5-ylamino)-quinazolin-6-yl]-benzyl}-6-aza-spiro(2.5]oct-1-yl)-methanol;

(6-{4-[4-(4-Phenoxy-phenylamino)-quinazolin-6-yl]-benzyl}-6-azaspiro[2.5]oct-1-yl)-methanol;

(5-{4-[4-(1-Benzenesulfonyl-1H-indol-5-ylamino)-quinazolin-6-yl]-benzyl}-5-aza-spiro[2.4]hept-1-yl)-methanol;

(5-{4-[4-(4-Phenoxy-phenylamino)-quinazolin-6-yl]-benzyl}-5-aza-spiro[2.4]hept-1 -yl)-methanol;

(5-{4-[4-(4-Phenoxy-phenylamino)-quinazolin-6-yl]-benzyl}-5-aza-spiro[2.5]oct-1-yl)-methanol;

and the pharmaceutically acceptable salts and solvates of the foregoing compounds.

This invention also relates to a method for the treatment of abnormal cell growth in a mammal, including a human, comprising administering to said mammal an amount of a compound of the formula 1, as defined above, or a pharmaceutically acceptable salt or solvate thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt or solvate thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt or solvate thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of preparing a compound of the formula 1

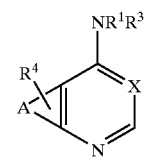

and to pharmaceutically acceptable salts and solvates thereof, wherein A, X, $R^1$, $R^4$ and $R^3$ are as defined above, which comprises either (a) reacting a compound of the formula 5 with a compound of the formula 6

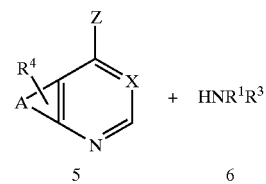

wherein Z is a leaving group and A, X, $R^1$, $R^3$, and $R^4$ are as defined above, or (b) reacting a compound of the formula 2 with a compound of the formula 6

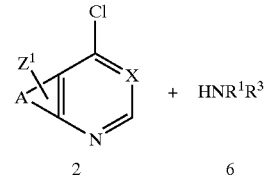

wherein X, A, $R^1$, and $R^3$ are as defined above and $Z^1$ is an activating group to provide an intermediate of the formula 7

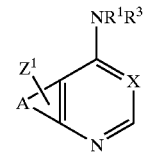

wherein $Z^1$, X, A, $R^1$, and $R^3$ are as defined above, and treating the compound of formula 7 with a coupling partner of the formula $X^1$—$(CR^1R^2)_t(C_6–C_{10}$ aryl) or $X^1$—$(CR^1R^2)_t$(4–10 membered heterocyclic), wherein t, $R^1$ and $R^2$ are as defined above as provided in the definition of $R^4$, the aryl and heterocyclic groups of the foregoing groups are substituted with a group that includes an aldehyde or acid moiety, and $X^1$ is —$B(OH)_2$ or —$Sn(C_1–C_5$ alkyl$)_3$, to provide a compound of formula 8

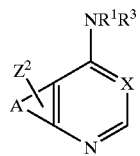

wherein X, A, R¹, and R³ are as defined above, and $Z^2$ is —$(CR^1R^2)_t(C_6-C_{10}$ aryl) or —$(CR^1R^2)_t$(4–10 membered heterocyclic), wherein t, R¹ and R² are as defined above as provided in the definition of R⁴, and the aryl and heterocyclic groups of the foregoing $Z^2$ groups are substituted with a group that includes an aldehyde or acid moiety, and modifying said acid or aldehyde moiety to introduce a group selected from —$(CR^1R^2)_qNR^1R^9$, —$(CR^1R^2)_qNR^9(C_1-C_6$ alkanoyl), —$(CR^1R^2)_qOR^9$, and —$(CR^1R^2)_qR^9$, wherein R¹, R², R⁹ and q are as defined above.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; and (4) any tumors that proliferate by receptor tyrosine kinases.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

In the compounds of formula 1, where terms such as $(CR^1R^2)_q$ or $(CR^1R^2)_t$ are used, R¹ and R² may vary with each iteration of q or t above 1. For instance, where q or t is 2 the terms $(CR^1R^2)_q$ or $(CR^1R^2)_t$ may equal —$CH_2CH_2$—, or —$CH(CH_3)C(CH_2CH_3)(CH_2CH_2CH_3)$—, or any number of similar moieties falling within the scope of the definitions of R¹ and R². Further, as noted above, any substituents comprising a $CH_3$ (methyl), $CH_2$ (methylene), or CH (methine) group which is not attached to a halogeno, SO or $SO_2$ group or to a N, O or S atom optionally bears on said group a substituent selected from hydroxy, $C_1$–$C_4$ alkoxy and —$NR^1R^2$.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

The subject invention also includes isotopically-labelled compounds, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

SCHEME 1

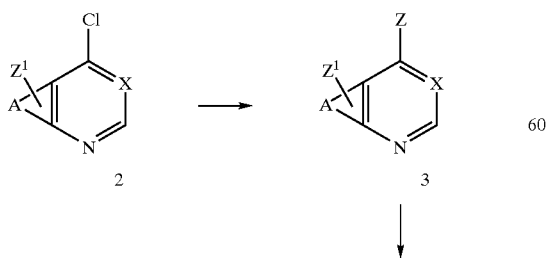

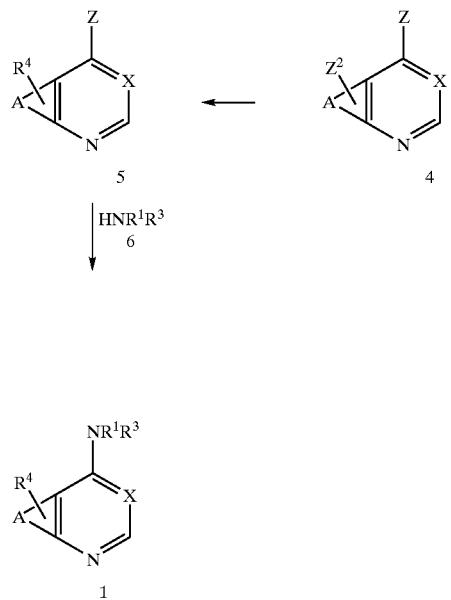

SCHEME 2

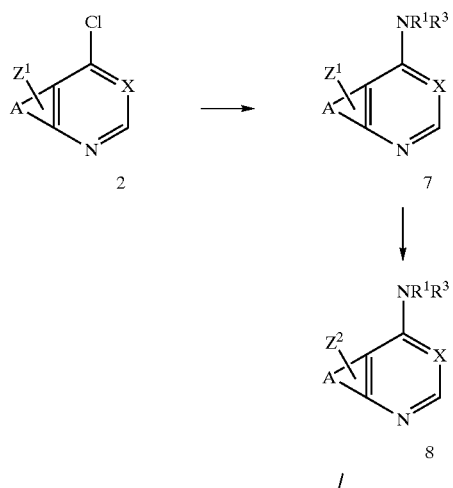

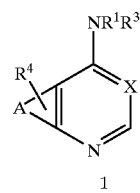

SCHEME 3

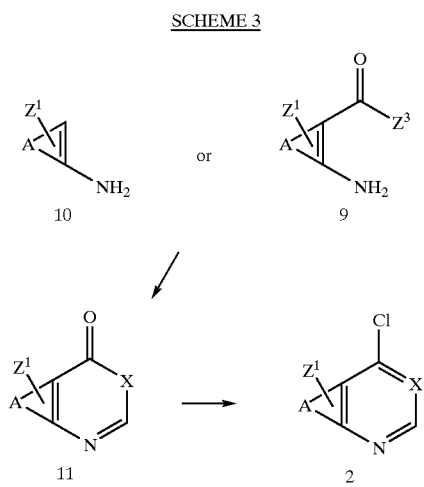

DETAILED DESCRIPTION OF THE INVENTION

General synthetic methods which may be referred to for preparing the compounds of the present invention are provided in U.S. Pat. No. 5,747,498 (issued May 5, 1998), U.S. patent application Ser. No. 08/953078 (filed Oct. 17, 1997), WO 98/02434 (published Jan. 22, 1998), WO 98/02438 (published Jan. 22, 1998), WO 96/40142 (published Dec. 19, 1996), WO 96/09294 (published Mar. 6, 1996), WO 97/03069 (published Jan. 30, 1997), WO 95/19774 (published Jul. 27, 1995) and WO 97/13771 (published Apr. 17, 1997). The foregoing patents and patent applications are incorporated herein by reference in their entirety. Certain starting materials may be prepared according to methods familiar to those skilled in the art and certain synthetic modifications may be done according to methods familiar to those skilled in the art. A standard procedure for preparing 6-iodoquinazolinone is provided in Stevenson, T. M., Kazmierczak, F., Leonard, N. J., J. Org. Chem. 1986, 51, 5, p. 616. Palladium-catalyzed boronic acid couplings are described in Miyaura, N., Yanagi, T., Suzuki, A. Syn. Comm. 1981, 11, 7, p. 513. Reduction of aromatic nitro groups can be performed by methods outlined in Brown, R. K., Nelson, N. A. J. Org. Chem. 1954, p. 5149; Yuste, R., Saldana, M, Walls, F., Tet. Lett. 1982, 23, 2, p. 147; or in WO/9609294, referred to above. Nitro substituted N1-phenylsulfonylindoles/indazoles can be prepared by the methods found in Sundberg, R. J., Bloom, J. D., J. Org. Chem. 1980, 45, 17, p. 3382; Ottoni, O. et al. Tetrahedron, 1998, 54, 13915; or Boger, Dale L. et. al.; J. Org. Chem; 55; 4; 1990; 1379. Substituted nitro N1-benzylindoles/indazoles can be prepared by methods found in Makosza, M.; Owczarczyk, Z.; J. Org. Chem., 54, 21, 1989, 5094; Adebayo, Adelaide T. O. M., Bowman, W. Russell, Salt, W. G., J. Chem. Soc. Perkin Trans.1, 1989, 1415; or WO 98/02434, referred to above. Benzyloxy-nitrobenzene intermediates may be prepared by methods found in WO 98/02434, referred to above.

Alternatively, arylmethoxy, or aryloxy nitrobenzene derivatives may be prepared from halo nitrobenzene precursors by nucleophilic displacement of the halide with an appropriate alcohol as described in Dinsmore, C. J. et al., Bioorg. Med. Chem. Lett., 7, 10, 1997, 1345; or Loupy, A. et al., Synth. Commun., 20, 18, 1990, 2855; or Brunelle, D. J. Tet. Lett., 25, 32, 1984, 3383. Fused and bridged bicyclic amines were synthesized according to the methods described in: Brighty, K. E. and Castaldi, M. J., Synlett, 1996, 1097; and Momose, T. et al., J. Chem. Soc. Perkin Trans. 1, 1997, 1307. Spirocyclic amines were synthesized according to methods found in WO 92122550. Starting materials, the synthesis of which is not specifically described herein or the published references referred to above, are either commercially available or can be prepared using methods well known to those of skill in the art.

In each of the reactions discussed or illustrated in the Schemes above, pressure is not critical unless otherwise indicated. Pressures from about 0.5 atmospheres to about 5 atmospheres are generally acceptable, and ambient pressure, i.e., about 1 atmosphere, is preferred as a matter of convenience.

Where the compound of formula 6, $HNR^1R^3$, is an optionally substituted indole or indoline moiety, such compounds may be prepared according to one or more methods known to those skilled in the art. Such methods are described in PCT international patent application publication number WO 95/23141 and in W. C. Sumpter and F. M. Miller, "Heterocyclic Compounds with Indole and Carbazole Systems," in volume 8 of "The Chemistry of Heterocyclic Compounds", Interscience Publishers Inc., New York (1954). Optional substituents may be included as appropriate before or after the coupling step illustrated in Scheme 1. Prior to the coupling step, primary and secondary amino moieties (other than said amine of formula 6, $HNR^1R^3$) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

With reference to Scheme 1 above, the compound of formula 1 may be prepared by coupling the compound of formula 5, wherein X, A, and $R^4$ are as defined above and Z is a leaving group, such as a phenoxy or a phenoxy derivative substituted with halo, cyano, nitro, or lower alkyl, with an amine of the formula 6, $HNR^1R^3$, wherein $R^1$ and $R^3$ are as defined above, in an anhydrous solvent, in particular a solvent selected from DMF (N,N-dimethylformamide), DME (ethylene glycol dimethyl ether), DCE (dichloroethane), t-butanol, and phenol, or a mixture of the foregoing solvents, a temperature within the range of about 50–150° C. for a period ranging from 1 to 48 hours. The compound of formula 6, $HNR^1R^3$, may be prepared by methods known to those skilled in the art, such as reduction of nitriles, reduction of imines or enamines, reduction of oximes, primary and secondary amides, reduction of a nitro group or reductive amination of either $R^1NH_2$ and $R^3CH(O)$ or $R^3NH_2$ and $R^1CH(O)$. The compound of formula 5 may be prepared by treating a compound of formula 4, wherein $Z^2$ is —$(CR^1R^2)_t(C_6-C_{10}$ aryl) or —$(CR^1R^2)_t$(4–10 membered heterocyclic), wherein t, $R^1$ and $R^2$ are as defined above as provided in the definition of $R^4$, and the aryl and heterocyclic groups of the foregoing groups are substituted by a group that includes an aldehyde or acid moiety that may be modified to introduce one or more groups selected from —$(CR^1R^2)_qNR^1R^9$, —$(CR^1R^2)_qNR^9(C_1-C_6$ alkanoyl), —$(CR^1R^2)_qOR^9$, and —$(CR^1R^2)_qR^9$ as provided in the definition of $R^4$ above. Such modifications may be done according to methods familiar to those skilled in the art For instance, an amine moiety may be introduced by reductive amination of an aldehyde group. A compound of the formula 4 can be obtained by treating a compound of the formula 3, wherein $Z^1$ is an activating group, such as bromo, iodo, —$N_2$, or —OTF (which is —$OSO_2CF_3$), with a coupling partner of the formula $X^1$—$(CR^1R^2)_t(C_6$–$C_{10}$ aryl) or $X^1$—$(CR^1R^2)_t$(4–10 membered heterocyclic), wherein t, $R^1$ and $R^2$ are as defined above as provided in the definition of $R^4$, the aryl and heterocyclic groups of the foregoing groups are substituted with a group that includes an aldehyde or acid moiety, and $X^1$ is —$B(OH)_2$ or —$Sn(C_1$–$C_5$ alkyl$)_3$. This reaction is generally done using palladium (0) or palladium (II) catalysts in a solvent such as DMF, THF (tetrahydrofuran), toluene, dioxanes, or a mixture of the foregoing solvents, at 60–100° C. for about 8–24 hours. The compound of formula 2 may be converted to the compound of formula 3 wherein Z is a substituted phenoxy derivative by treating the starting compound with an appropriate metal phenoxide, such as sodium phenolate, in a solvent, such as DMF or phenol, at a temperature ranging from about 0° C. to 100° C. for a period ranging from about 2 to 24 hours.

In the alternative, compounds of the formula 1 may be prepared according to the synthesis outlined in Scheme 2. In Scheme 2, a compound of the formula 1 may be obtained by treating a compound of formula 8, wherein $Z^2$ is as defined above, as described above regarding the conversion of the compound of formula 4 to a compound of formula 5. A compound of the formula 8 may be obtained by treating a compound of formula 7, wherein $Z^1$ is an activating group as defined above, as described above regarding the conversion of the compound of formula 3 to a compound of formula 4. A compound of formula 7 may be obtained from a compound of formula 2 by reaction with an amine of the formula 6, $HNR^1R^3$, wherein $R^1$ and $R^3$ are as defined above, in a anhydrous solvent, in particular a solvent selected from DMF, DME, DCE, t-butanol, and phenol, or a mixture of the foregoing solvents, a temperature within the range of about 50–150° C. for a period ranging from about 1 to 48 hours.

The starting compound of formula 2 may be prepared as illustrated in Scheme 3. In Scheme 3, the compound of formula 11 wherein X is NH may be prepared from a compound of formula 9, wherein A and $Z^1$ are as defined above and $Z^3$ is OH, according to one or more procedures described in WO 95/19774, referred to above, and a compound of formula 11 wherein X is CH may be prepared from a compound of formula 10, wherein A and $Z^1$ are as defined above, according to procedures described in WO 95/19774, referred to above. The compound of formula 11 may be converted to the compound of formula 2 by treating the starting compound with a chlorinating reagent, such as $POCl_3$ or ClC(O)C(O)Cl/DMF in a halogenated solvent at a temperature ranging from about 60° C. to 150° C. for a period ranging from about 2 to 24 hours.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are potent inhibitors of the erbB family of oncogenic and protoonocogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formula 1 may be determined by the following procedure.

The c-erbB2 kinase assay is similar to that described previously in Schrang et. al. Anal. Biochem. 211, 1993, p233–239. Nunc MaxiSorp 96-well plates are coated by incubation overnight at 37° C. with 100 mL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 50 mL of 50 mM HEPES (pH 7.5) containing 125 mM sodium chloride, 10 mM magnesium chloride, 0.1 mM sodium orthovanadate, 1 mM ATP, 0.48 mg/mL (24 ng/well) c-erbB2 intracellular domain. The intracellular domain of the erbB2 tyrosine kinase (amino acids 674–1255) is expressed as a GST fusion protein in Baculovirus and purified by binding to and elution from glutathione coated beads. The compound in DMSO (dimethylsulfoxide) is added to give a final DMSO concentration of about 2.5%. Phosphorylation was initiated by addition of ATP (adenosine triphosphate) and proceeded for 6 minutes at room temperature, with constant shaking. The kinase reaction is terminated by aspiration of the reaction mixture and subsequent washing with wash buffer (see above). Phosphorylated PGT is measured by 25 minutes of incubation with 50 mL per well HRP-conjugated PY54 (Oncogene Science Inc. Uniondale, N.Y.) antiphosphotyrosine antibody, diluted to 0.2 mg/mL in blocking buffer (3% BSA and 0.05% Tween 20 in PBS). Antibody is removed by aspiration, and the plate is washed 4 times with wash buffer. The colorimetric signal is developed by addition of TMB Microwell Peroxidase Substrate (Kirkegaard and Perry, Gaithersburg, Md.), 50 mL per well, and stopped by the addition of 0.09 M sulfuric acid, 50 mL per well. Phosphotyrosine is estimated by measurement of absorbance at 450 nm. The signal for controls is typically 0.6–1.2 absorbance units, with essentially no background in wells without the PGT substrate and is proportional to the time of incubation for 10 minutes. Inhibitors were identified by reduction of signal relative to wells without inhibitor and $IC_{50}$ values corresponding to the concentration of compound required for 50% inhibition are determined.

The activity of the compounds of formula 1, in vivo, can be determine by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res., 35, 2434–2439 (1975) and Corbett T. H., et al., "A Mouse Colon-tumor Model for Experimental Therapy", Cancer Chemother. Rep. (Part 2)", 5, 169–186 (1975), with slight modifications. Tumors are induced in the left flank by subcutaneous (sc) injection of 1–5 million log phase cultured tumor cells (murine FRE-ErbB2 cells or human SK-OV3 ovarian carcinoma cells) suspended in 0.1 ml RPMI 1640 medium. After sufficient time has elapsed for the tumors to become palpable (100–150 mm3 in size/5–6 mm in diameter) the test animals (athymic female mice) are treated with test compound (formulated at a concentration of 10 to 15 mg/ml in 5 Gelucire) by the intraperitoneal (ip) or oral (po) route of administration once or twice daily for 7 to 10 consecutive days. In order to determine an anti-tumor effect, the tumor is measured in millimeters with a Vernier caliper across two diameters and the tumor size (mm3) is calculated using the formula: Tumor size (mm3)=(length× [width]2)/2, according to the methods of Geran, R. I., et al. "Protocols for Screening Chemical Agents and Natural Products Against Animal Tumors and Other Biological Systems", Third Edition, Cancer Chemother. Rep., 3, 1–104 (1972). Results are expressed as percent inhibition, according to the formula: Inhibition (%)=$(TuW_{control}-TuW_{test})$ $TuW_{control} \times 100\%$. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other ant-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art For examples, see *Remington's Pharmaceutical Sciences,* Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples, "Ac" means acetyl, "Et" means ethyl, "Me" means methyl, and "Bu" means butyl.

Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 systemA gradient solvent method is used-running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 ml/minute.

METHOD A

Synthesis of (3-{4-[4-(1-Cyclopropylmethyl-1H-indol-5-ylamino)-guinazolin6-yl]-benzyl}-3-aza-bicyclo[3.1.0]hex-6-yl)-methanol (18) 6-Iodo-4quinazolinone (12)

A solution of 2-amino-5-iodobenzoic acid (26.3 g, 100 mmol) and formamidine acetate (13.5 g, 130 mmol) in ethanol (400 mL) was refluxed for 20 hours. After cooling to 0° C., the solid product was collected by filtration. Further drying in vacuo provided 6-iodo4-quinazolinone 12 (22.0 g, 81%) as a grey crystalline solid. 1H NMR (400 MHz; DMSO-$d_6$) δ: 12.38 (br. s, 1H), 8.35 (d, 1H), 8.05–8.10 (m, 2H), 7.43 (dd, 1H). LRMS: 272.9 (MH+).

6-iodo-4-chloroquinazoline (13)

To a stirred solution of DMF (N,N-dimethylformamide) (6.3 mL) in DCE (dichloroethane) (20 mL) cooled to 0° C. was added dropwise a solution of oxalyl chloride (60 mL of a 2M solution in DCE). After addition was complete, the cooling bath was removed and 6-iodo-3H-quinazolinone 12 (10 g, 36.8 mmol) was added as a solid. The resulting mixture was heated to reflux under nitrogen for 3 hours. Upon cooling to room temperature, the reaction was quenched cautiously with $H_2O$. $CH_2Cl_2$ was added and the bilayer transferred to a separatory funnel. The aqueous layer was extracted with $CH_2Cl_2$ (2×50 mL) and the combined organic layers dried ($Na_2SO_4$). The solvent was removed in vacuo to provide a yellow solid which was triturated with diethyl ether to remove any remaining impurities. The resulting yellow solid obtained by filtration was shown to be pure by NMR. For compound 13: $^1$HNMR (CDCl$_3$, 400 MHz): δ: 9.05 (s, 1H), 8.65 (d, 1H), 8.21 (dd, 1H), 7.78 (d, 1H).

6-iodo-4-phenoxyquinazoline (14)

A suspension of NaH (washed free of mineral oil) in DMF (40 mL) was cooled to 0° C. and a solution of phenol (5.65 g, 60 mmol) in DMF (20 mL) was added dropwise. Upon completion of addition, 6-iodo-4-chloroquinazoline 13 (14.6 g, 50.3 mmol) was added as a solid in small portions. The cooling bath was moved and the reaction mixture was stirred at room temperature for 2 hours. The mixture was then quenched with water (200 mL), diluted with EtOAc (300 mL) and transferred to a separatory funnel. The organic layer was washed with dilute aqueous NaOH, water and brine and dried over $Na_2SO_4$. Filtration of the solids and removal of the solvent provided 6-iodo4-phenoxyquinazoline 14 (17.2 g, 98%) as a yellow solid. $^1$H NMR (400 MHz; CDCl$_3$): δ: 8.74 (d, 1H), 8.14 (s, 1H), 8.12 (dd, 1H), 7.71 (d, 1H). 7.49 (dd, 2H), 7.32 (t, 1H), 7.22 (m, 2H).

4-(4-Phenoxy-quinazolin-6-yl)benzaldehyde (15)

To a solution of toluene (211 mL) in a 1.0 L round-bottom flask equipped with a reflux condenser was added 1,4-bis (diphenyl)phosphino)-butane (1.22 g, 2.87 mmol) and bis (benzonitrile)dichloro-palladium (1.1 g, 2.87 mmol). The resulting solution was stirred at room temperature for 30 minutes followed by the addition of THF (tetrahydrofuran) (255 mL) and EtOH (115 mL). To the resulting mixture was added 6-iodo-4-phenoxy-quinazoline 14 (5.0 g, 14.4 mmol), 4-formylphenylboronic acid (4.3 g, 28.7 mmol) and aqueous 1M $Na_2CO_3$ (29 mL). The mixture was heated at reflux under an atmosphere of $N_2$ for 18 hours. The reaction mixture was filtered hot and the solvent removed under reduced pressure. The residue was taken up in CHCl$_3$ and washed with water, brine, and dried (MgSO$_4$). The solvent was removed under reduced pressure and the residue was purified using flash chromatography (silica gel, EtOAc/hexanes 4:6) to provide (4.42 g, 13.54 mmol) 4-(4-phenoxy-quinazolin-6-yl)benzaldehyde 15 in 94% yield. $^1$H NMR (CDCl$_3$ ) δ7.26 (m, 3H), 2.88 (m, 1H), 7.51 (M, 2H), 7.92 (d, 2H, J=8.4 Hz), 8.02 (d, 2H, J=8 Hz), 8.11 (d, 1H, J=8.8 Hz), 8.20 (dd, 1H, J=2.4 and 8.8 Hz), 8.63 (d, 1H, J=2.4 Hz), 8.79 (s, 1H); MS (Cl) m/e 326 (M$^+$+1, 100).

3-[4-(4-Phenoxy-quinazolin6-yl)-benzyl]-3-aza-bicyclo[3.1.0]hex-6-yl)-methanol (16)

To a solution of 1:1 CHCl$_3$ and MeOH in a round-bottom flask under $N_2$ was added (3-aza-bicyclo[3.1.0]hex6-yl)-methanol 17 (2.27 g, 19.7 mmol) which was allowed to stir at room temperature for fifteen minutes. To the amine solution was added 4-(4-phenoxyquinazolin-6yl) benzaldehyde 15 (3.78 g, 11.6 mmol) followed by the dropwise addition of acetic acid until the pH was approximately 6. NaCNBH$_3$ was added to the reaction mixture which was then allowed to stir overnight at room temperature under an atmosphere of N$_2$. The solution was diluted with CHCl$_3$ and washed 3× with aqueous NaHCO$_3$ until the pH was approximately 9. The organic layer was separated, dried (MgSO$_4$) and removed under reduced pressure to provide a yellow viscous oil. The residue was purified by flash chromatography (silica gel, EtOAc-5%MeOH/EtOAc) to provide (3.51 g, 8.28 mmol) compound 16 as a white solid in 71% yield. For compound 16: $^1$H NMR (CDCl$_3$) δ8.75 (s, 1H), 8.54 (d, 1H J=2 Hz), 8.17 (dd, 1H J=8.4 and 2.4 Hz), 8.05 (d, 1H, J=8.4 Hz), 7.66 (d, 2H, J=8 Hz), 7.48 (m, 2H), 7.39 (m, 2H), 7.32 (m, 1H), 7.25 (m, 2H), 3.65 (s, 2H), 3.44 (d, 2H, J=3.6 Hz), 3.02 (d, 2H, J=8.8 Hz), 2.38 (d, 2H, J=8.4 Hz), 1.62 (m, 1H), 1.30 (s, 2H); MS (Cl) m/e 423 (M$^+$+1, 100).

(3-{-4-[4-(1-Cyclopropylmethyl-1H-indol-5-ylamino)-quinazolin-6-yl]-benzyl}-3-aza-bicyclo [3.1.0]hex-6-yl)methanol (18)

To a 3 mL Wheaton vial was, added {3-[4-(4-phenoxy-quinazolin-6-yl)-benzyl}-3-aza-bicyclo[3.1.0]hex-6-yl)-methanol 16 (100 mg, 0.24 mmol), 1-cyclopropylmethyl-1H-indol-5-ylamine 19 (48 mg, 0.26 mmol), pyridinium hydrochloride (33 mg, 0.284 mmol), and phenol (155 mg, 1.652 mmol). The vial was capped and heated overnight at 110° C. The vial was cooled to room temperature and the residue taken up in CHCl$_3$ and washed with 15% aqueous NaOH, water, brine, and dried (MgSO$_4$). The solvent was removed and the residue purified by flash chromatography (silica gel, EtOAc:MeOH, 95:5) to provide compound 18 (88 mg, 0.159 mmol) as a light brown solid in 67% yield. For compound 18: MS (Cl) m/e 515 (M$^+$+1, 100); HPLC, rt=4.83 min.

METHOD B

Synthesis of 8-{4-[4-(1-Benzenesulfonyl-1H-indol-5-ylamino)-quinazolin-6-yl]-benzyl}-8-aza-bicyclo [3.2.1]octan-3-ol (1-Benzenesulfonyl-1H-indol-5-yl)-(6-iodo-quinazolin4-yl)-amine (20)

6-iodo-4-chloroquinazoline 13 (2.38 g, 8.20 mmol) and 5-amino-1-benzenesulfonylindole 21 (2.46 g, 9.00 mmol) were combined in DCE (20 mL) and t-butanol (20 mL). The resulting mixture was heated at reflux under nitrogen for 18 hours to form a bright yellow suspension. Upon cooling the solids were filtered and rinsed with CH$_2$Cl$_2$ and placed under high vacuum to remove any excess solvent. The title compound (3.23 g, 75%) was obtained as a yellow solid. For compound 20: $^1$H NMR (DMSO-d$_6$; 400 MHz): δ: 10.05 (s, 2H,), 8.93 (s, 1H), 8.53 (s, 1H), 8.25 (m, 1H,), 8.10 (m, 5H), 7.97 (m, 3H), 7.82 (m, 2H), 7.70 (m, 2H), 7.65 (m, 2H), 6.88 (d, 1H, J=3.57 Hz).

4-[4-(1-Benzenesulfonyl-1H-indol-5-ylamino)-guinazolin-6-yl]-benzaldehyde (22)

To a solution of toluene (100 mL) in a 500 mL round-bottom flask equipped with a reflux condenser was added 1,4-bis(diphenyl)phosphino)-butane (4.25 mg, 0.997 mmol) and bis(benzonitrile)dichloro-palladium (385 g, 0.997 mmol). Nitrogen was bubbled through the reaction mixture for 1 minute and the resulting suspension was stirred at room temperature for 30 minutes. THF (125 mL) and EtOH (50 mL) were then added. To the resulting mixture was added (1-benzenesulfonyl-1H-indol-5-yl)-(6-iodo-quinazolin-4-yl)-amine 20 (3.5 g, 6.6 mmol), 4-formylphenylboronic acid (1.99 g, 13.3 mmol) and 2M aq Na$_2$CO$_3$ (6.7 mL). The mixture was heated at reflux under an atmosphere of N$_2$ for 15 hours. The solvent was removed under reduced pressure and the residue was purified using flash chromatography (silica gel, EtOAc/hexanes 1:1) to provide 3.1 g of 4-[4-(1-benzenesulfonyl-1H-indol-5-ylamino)-quinazolin-6-yl]-benzaldehyde 22 in 92% yield. $^1$H NMR (DMSO-d$_6$; 400 MHz): δ: 9.24 (s, 1H, NH), 8.84 (s, 1H), 8.33 (dd, 1H, J=8.9 Hz and 1.7 Hz), 8.01 (m, 4H), 7.90 (m, 2H), 7.70 (m, 2H), 7.60 (m, 3H), 6.92 (dd, 1H, J=3.7 Hz and 0.6 Hz); MS (Cl) m/e 505.1 (M$^+$+1, 100).

8-{4-[4-(1-Benzenesulfonyl-1H-indol-5-ylamino)-quinazolin-6-yl]-benzyl}-8-aza-bicyclo[3.2.1]octan-3-ol (23)

To a solution of CHCl$_3$ (1.5 mL) and MeOH (3 mL) in a round-bottom flask under N$_2$ was added 8-aza-bicyclo [3.2.1]octan-3-ol 24 (70 mg, 0.495 mmol). AcOH was added to adjust the pH to 5. To the amine solution was added 4-[4-(1-benzenesulfonyl-1H-indol-5-ylamino)-quinazolin-6-yl]-benzaldehyde 22 (100 mg, 0.198 mmol) and the resulting solution was stirred at room temperature for 3 hours. NaCNBH$_3$ was added to the reaction mixture which was then allowed to stir overnight at room temperature under an atmosphere of N$_2$. The solution was diluted with CH$_2$Cl$_2$ and poured into 1N NaOH (10 mL). The aqueous layer was separated and extracted with another 2×15 mL of CH$_2$Cl$_2$. The organic layers were dried (MgSO$_4$) and the solvent was removed under reduced pressure to provide a yellow viscous oil. The residue was purified by flash chromatography (silica gel, CH$_2$Cl$_2$-10%MeOH/CH$_2$Cl$_2$) to provide 45 mg of compound 23 as a white solid in 36% yield. HPLC, rt=5.25 min; MS (Cl) m/e 616.2 (M$^+$+1, 100).

The following examples were prepared following either method A or method B as described above. In the Table, the term "min" refers to minutes.

| Example Number | Method of preparation | IUPAC name | LRMS (MH+) | HPLC |
|---|---|---|---|---|
| 1 | A | {6-[4-(6-Amino-3-aza-bicyclo[3.1.0]hex-3-ylmethyl)-phenyl]-quinazolin-4-yl}-(1-benzenesulfonyl-1H-indol-5-yl)-amine | 587.2 | 7.99 min |
| 2 | A | {6-[4-(6-Amino-3-aza-bicyclo[3.1.0]hex-3-ylmethyl)-phenyl]-quinazolin-4-yl}-(4-benzyl-phenyl)-amine | 498.3 | 5.09 min |

-continued

| Example Number | Method of preparation | IUPAC name | LRMS (MH+) | HPLC |
|---|---|---|---|---|
| 3 | A | {6-[4-(6-Amino-3-aza-bicyclo[3.1.0]hex-3-ylmethyl)-phenyl]-quinazolin-4-yl}-(4-phenoxy-phenyl)-amine | 500.3 | 4.93 min |
| 4 | A | (3-{4-[4-(4-Benzyl-phenylamino)-quinazolin-6-yl]-benzyl}-3-aza-bicyclo[3.1.0]hex-6-yl)-methanol | 513.2 | 5.44 min |
| 5 | A | (3-{4-[4-(4-Phenoxy-phenylamino)-quinazolin-6-yl]-benzyl}-3-aza-bicyclo[3.1.0]hex-6-yl)-methanol | 515.4 | 5.27 min |
| 6 | A | (3-{4-[4-(1-Benzenesulfonyl-1H-indol-5-ylamino)-quinazolin-6-yl]-benzyl}-3-aza-bicyclo[3.1.0]hex-6-yl)-methanol | 602.3 | 5.17 min |
| 7 | B | (6-{4-[(1-Aza-bicyclo[2.2.2]oct-3-ylamino)-methyl]-phenyl}-quinazolin-4-yl)-(4-phenoxy-phenyl)-amine | 526.4 | 5.43 min |
| 8 | B | (6-{4-[(1-Aza-bicyclo[2.2.2]oct-3-ylamino)-methyl]-phenyl}-quinazolin-4-yl)-(4-benzyl-phenyl)-amine | 526.4 | 5.52 min |
| 9 | B | (6-{4-[(1-Aza-bicyclo[2.2.2]oct-3-ylamino)-methyl]-phenyl}-quinazolin-4-yl)-(1-benzenesulfonyl-1H-indol-5-yl)-amine | 613.4 (−) | 5.33 min |
| 10 | B | (6-{4-[(3-Aza-bicyclo[3.1.0]hex-6-ylamino)-methyl]-phenyl}-quinazolin-4-yl)-(4-phenoxy-phenyl)-amine | 500.3 | 4.93 min |
| 11 | B | (6-{4-[(3-Aza-bicyclo[3.1.0]hex-6-ylamino)-methyl]-phenyl}-quinazolin-4-yl)-(4-benzyl-phenyl)-amine | 498.3 | 5.10 min |
| 12 | B | 3-{4-[4-(4-Benzyl-phenylamino)-quinazolin-6-yl]-benzylamino}-8-methyl-8-aza-bicyclo[3.2.1]octan-6-ol | 558.3 | 4.47 min/5.77 min diastereomer |
| 13 | B | (6-{4-[(3-Aza-bicyclo[3.1.0]hex-6-ylamino)-methyl]-phenyl}-quinazolin-4-yl)-(1-benzenesulfonyl-1H-indol-5-yl)-amine | 587.2 | 4.80 min |
| 14 | A | (4-Benzyl-phenyl)-{6-[4-(6-methoxymethyl-3-aza-bicyclo[3.1.0]hex-3-ylmethyl)-phenyl]-quinazolin-4-yl}-amine | 527.3 | 6.06 min |
| 15 | A | {6-[4-(6-Methoxymethyl-3-aza-bicyclo[3.1.0]hex-3-ylmethyl)-phenyl]-quinazolin-4-yl}-(4-phenoxy-phenyl)-amine | 529.4 | 5.86 min |
| 16 | A | (1-Benzenesulfonyl-1H-indol-5-yl)-{6-[4-(6-methoxymethyl-3-aza-bicyclo[3.1.0]hex-3-ylmethyl)-phenyl]-quinazolin-4-yl}-amine | 616.2 | 5.64 min |
| 17 | B | (3-{4-[4-(4-Phenoxy-phenylamino)-quinazolin-6-yl]-benzylamino}-bicyclo[2.2.1]hept-2-yl)-methanol | 543.3 | 5.93 min |
| 18 | B | (3-{4-[4-(4-Benzyl-phenylamino)-quinazolin-6-yl]-benzylamino}-bicyclo[2.2.1]hept-2-yl)-methanol | 541.3 | 6.15 min |
| 19 | B | (3-{4-[4-(1-Benzenesulfonyl-1H-indol-5-ylamino)-quinazolin-6-yl]-benzylamino}-bicyclo[2.2.1]hept-2-yl)-methanol | 630.2 | 5.78 min |
| 20 | A | (4-Benzyl-phenyl)-(6-{4-[(8-methyl-8-aza-bicyclo[3.2.1]oct-3-ylamino)-methyl]-phenyl}-quinazolin-4-yl)-amine | 540.4 | 5.97 min |
| 21 | A | (6-{4-[(8-Methyl-8-aza-bicyclo[3.2.1]oct-3-ylamino)-methyl]-phenyl}-quinazolin-4-yl)-(4-phenoxy-phenyl)-amine | 542.3 | 5.76 min |
| 22 | A | (1-Benzenesulfonyl-1H-indol-5-yl)-(6-{4-[(8-methyl-8-aza-bicyclo[3.2.1]oct-3-ylamino)-methyl]-phenyl}-quinazolin-4-yl)-amine | 629.2 | 5.60 min |
| 23 | A | (3-{4-[4-(4-[1,2,3]Thiadiazol-5-yl-phenylamino)-quinazolin-6-yl]-benzyl}-3-aza-bicyclo[3.1.0]hex-6-yl)-methanol | 507.3 | 4.41 min |
| 24 | A | (3-{4-[4-(4-Cyclohexyl-phenylamino)-quinazolin-6-yl]-benzyl}-3-aza-bicyclo[3.1.0]hex-6-yl)-methanol | 505.4 | 6.11 min |
| 25 | B | 8-Methyl-3-{4-[4-(4-phenoxy-phenylamino)-quinazolin-6-yl]-benzylamino}-8-aza-bicyclo[3.2.1]octan-6-ol | 558.3 | 5.64 min |

-continued

| Example Number | Method of preparation | IUPAC name | LRMS (MH+) | HPLC |
|---|---|---|---|---|
| 26 | B | 3-{4-[4-(1-Benzyl-1H-indol-5-ylamino)-quinazolin-6-yl]-benzylamino}-8-methyl-8-aza-bicyclo[3.2.1]octan-6-ol | 595.3 | 5.44 min |
| 27 | B | 3-{4-[4-(1-Benzenesulfonyl-1H-indol-5-ylamino)-quinazolin-6-yl]-benzylamino}-8-methyl-8-aza-bicyclo[3.2.1]octan-6-ol | 645.3 | 5.53 min |
| 28 | A | (3-{4-[4-(4-p-Tolyloxy-phenylamino)-quinazolin-6-yl]-benzyl}-3-aza-bicyclo[3.1.0]hex-6-yl)-methanol | 529.4 | 5.63 min |
| 29 | A | (3-{4-[4-(Biphenyl-4-ylamino)-quinazolin-6-yl]-benzyl}-3-aza-bicyclo[3.1.0]hex-6-yl)-methanol | 499.3 | 5.36 min |
| 30 | A | (3-{4-[4-(4-Ethyl-phenylamino)-quinazolin-6-yl]-benzyl}-3-aza-bicyclo[3.1.0]hex-6-yl)-methanol | 451.3 | 4.73 min |
| 31 | A | 4-{6-[4-(6-Hydroxymethyl-3-aza-bicyclo[3.1.0]hex-3-ylmethyl)-phenyl]-quinazolin-4-ylamino}-N-phenyl-benzamide | 542.2 | 4.30 min |
| 32 | A | N,N-Diethyl-3-{6-[4-(6-hydroxymethyl-3-aza-bicyclo[3.1.0]hex-3-ylmethyl)-phenyl]-quinazolin-4-ylamino}-benzamide | 522.3 | 4.05 min |
| 33 | A | [3-(4- {4-[3-Methyl-4-(pyridin-2-ylmethoxy)-phenylamino]-quinazolin-6-yl}-benzyl)-3-aza-bicyclo[3.1.0]hex-6-yl]-methanol | 544.3 | 4.41 min |
| 34 | A | (3-{4-[4-(4-Benzyloxy-phenylamino)-quinazolin-6-yl]-benzyl}-3-aza-bicyclo[3.1.0]hex-6-yl)-methanol | 529.3 | 5.21 min |
| 35 | A | [3-(4-{4-[1-(Propane-2-sulfonyl)-1H-indol-5-ylamino]-quinazolin-6-yl}-benzyl)-3-aza-bicyclo[3.1.0]hex-6-yl]-methanol | 568.3 | 4.73 min |
| 36 | B | 8-Methyl-3-(4-{4-[1-(propane-2-sulfonyl)-1H-indol-5-ylamino]-quinazolin-6-yl}-benzylamino)-8-aza-bicyclo[3.2.1]octan-6-ol | 611.2 | 5.10 min |
| 37 | A | (3-{4-[4-(1-Benzenesulfonyl-2-methyl-1H-indol-5-ylamino)-quinazolin-6-yl]-benzyl}-3-aza-bicyclo[3.1.0]hex-6-yl)-methanol | 616.2 | 5.47 min |
| 38 | A | (3-{4-[4-(1-Benzyl-1H-indazol-5-ylamino)-quinazolin-6-yl]-benzyl}-3-aza-bicyclo[3.1.0]hex-6-yl)-methanol | 553.3 | 4.69 min |
| 39 | A | (3-{4-[4-(1-Methanesulfonyl-1H-indol-5-ylamino)-quinazolin-6-yl]-benzyl}-3-aza-bicyclo[3.1.0]hex-6-yl)-methanol | 540.2 | 4.21 min |
| 40 | A | (3-{4-[4-(1-Ethanesulfonyl-1H-indol-5-ylamino)-quinazolin-6-yl]-benzyl}-3-aza-bicyclo[3.1.0]hex-6-yl)-methanol | 554.2 | 4.47 min |
| 41 | B | (1-Benzenesulfonyl-1H-indol-5-yl)-(6-{4-[(3-oxa-bicyclo[3.1.0]hex-6-ylamino)-methyl]-phenyl≡-quinazolin-4-yl)-amine | 588.2 | 5.61 min |
| 42 | B | 8-{4-[4-(1-Benzenesulfonyl-1H-indol-5-ylamino)quinazolin-6-yl]-benzyl}-8-aza-bicyclo[3.2.1]octan-3-ol | 616.2 | 5.25 min |
| 43 | B | 8-(4-{4-[1-(Propane-2-sulfonyl)-1H-indol-5-ylamino]-quinazolin-6-yl}-benzyl)-8-aza-bicyclo[3.2.1]octan-3-ol | 582.2 | 4.84/4.96 min |
| 44 | B | 8-{4-[4-(4-Phenoxy-phenylamino)-quinazolin-6-yl]-benzyl}-8-aza-bicyclo[3.2.1]octan-3-ol | 529.3 | 5.35 min |
| 45 | B | 8-{4-[4-(1-Benzyl-1H-indol-5-ylamino)-quinazolin-6-yl]-benzyl}-8-aza-bicyclo[3.2.1]octan-3-ol | 566.3 (+) | 5.23 min |
| 46 | A | (3-{5-[4-(4-Phenoxy-phenylamino)-quinazolin-6-yl]-pyridin-2-ylmethyl}-3-aza-bicyclo[3.1.0]hex-6-yl)-methanol | 516.2 | 5.04 min |
| 47 | A | (3-{5-[4-(1-Benzenesulfonyl-1H-indol-5-ylamino)-quinazolin-6-yl]-pyridin-2-ylmethyl}-3-aza-bicyclo[3.1.0]hex-6-yl)-methanol | 603.2 | 4.98 min |
| 48 | A | (3-{5-[4-(1-Benzyl-1H-indazol-5-ylamino)-quinazolin-6-yl]-pyridin-2-ylmethyl}-3-aza-bicyclo[3.1.0]hex-6-yl)- | 554.2 | 4.48 min |

-continued

| Example Number | Method of preparation | IUPAC name | LRMS (MH+) | HPLC |
|---|---|---|---|---|
| 49 | A | methanol (3-{4-[4-(6-Phenoxy-pyridin-3-ylamino)-quinazolin-6-yl]-benzyl}-3-aza-bicyclo[3.1.0]hex-6-yl)-methanol | 516.2 | 4.74 min |
| 50 | A | (3-{5-[4-(4-Benzyloxy-phenylamino)-quinazolin-6-yl]-pyridin-2-ylmethyl}-3-aza-bicyclo[3.1.0]hex-6-yl)-methanol | 530.2 | 4.98 min |
| 51 | A | [3-(5-{4-[3-Methyl-4-(pyridin-2-ylmethoxy)-phenylamino]-quinazolin-6-yl}-pyridin-2-ylmethyl)-3-aza-bicyclo[3.1.0]hex-6-yl]-methanol | 545.2 | 4.15 min |
| 52 | A | (3-{5-[4-(4-Benzyl-phenylamino)-quinazolin-6-yl]-pyridin-2-ylmethyl}-3-aza-bicyclo[3.1.0]hex-6-yl)-methanol | 514.3 | 5.18 min |
| 53 | A | {3-[4-(4-Phenoxy-phenylamino)-quinazolin-6ylmethyl]-3-aza-bicyclo[3.1.0]hex-6-yl}methanol | 452.3 | 7.95 min |
| 54 | B | (5-{4-[4-(1-Benzenesulfonyl-1H-indol-5-ylamino)-quinazolin-6-yl]-benzyl}-5-aza-spiro[2.5]oct-1-yl)-methanol | 630.1 | 5.43 min |
| 55 | B | (5-{4-[4-(4-Phenoxy-phenylamino)-quinazolin-6-yl]-benzyl}-5-aza-spiro[2.5]oct-1-yl)-methanol | 543.2 | 5.59 min |
| 56 | B | (6-{4-[4-(1-Benzenesulfonyl-1H-indol-5-ylamino)-quinazolin-6-yl]-benzyl}-6-aza-spiro[2.5]oct-1-yl)-methanol | 630.2 | 5.36 min |
| 57 | B | (6-{4-[4-(4-Phenoxy-phenylamino)-quinazolin-6-yl]-benzyl}-6-azaspiro[2.5]oct-1-yl)-methanol | 543.2 | 5.53 min |
| 58 | B | (5-{4-[4-(1-Benzenesulfonyl-1H-indol-5-ylamino)-quinazolin-6-yl]-benzyl}-5-aza-spiro[2.4]hept-1-yl)-methanol | 616.1 | 5.34 min |
| 59 | B | (5-{4-[4-(4-Phenoxy-phenylamino)-quinazolin-6-yl]-benzyl}-5-aza-spiro[2.4]hept-1-yl)-methanol | 529.4 (+) | 5.50 min |
| 60 | B | (5-{4-[4-(4-Phenoxy-phenylamino)-quinazolin-6-yl]-benzyl}-5-aza-spiro[2.5]oct-1-yl)-methanol | 543.2 | 5.91 min |

The following compounds (and their pharmaceutically acceptable salts and solvates, and all stereoisomers including any endo and exo isomers) which are part of the present invention, may be prepared using the methods described above and/or methods familiar to those skilled in the art:

(3-{4-[4-(3-Fluoro-4-phenoxy-phenylamino)-quinazolin6-yl]-benzyl}-3-aza-bicyclo[3.1.0]hex6-yl)-methanol;

(3-{4-[4-(4-Phenoxy-3-trifluoromethyl-phenylamino)-quinazolin-6-yl]-benzyl}-3-aza-bicyclo[3.1.0]hex-6-yl)-methanol;

(3-{4-[4-(3-Chloro4-phenoxy-phenylamino)-quinazolin6-yl]-benzyl}-3-aza-bicyclo[3.1.0]hex4-yl)-methanol;

(5-{4-[4-(1 -Benzenesulfonyl-1H-indol-5-ylamino)-quinazolin6-yl]-benzyl}-5-aza-spiro[2.5]oct-1-yl)-methanol;

8-{4-[4-(1-Benzenesulfonyl-1H-indol-5-ylamino)-quinazolin-6-yl]-benzyl}-8-aza-bicyclo[3.2.1]octan-3-ol;

8-{4-[4-(1-Benzyl-1H-indol-5-ylamino)-quinazolin6-yl]-benzyl}-8-aza-bicyclo[3,2.1]octan-3-ol;

8-{4-[4-(3-Chloro4-phenoxy-phenylamino)-quinazolin6-yl]-benzyl}-8-aza-bicyclo[3.2.1]octan-3-ol;

8-{4-[4-(3-Methyl4-phenoxy-phenylamino)-quinazolin6-yl]-benzyl}-8-aza-bicyclo[3.2.1]octan-3-ol;

8-(4-{4-[1-(Propane-2-sulfonyl)-1H-indol-5-ylamino]-quinazolin6-yl}-benzyl)-8-aza-bicyclo[3.2.1]octan-3-ol;

(3-{4-[4-(4-Benzyloxy-3-methyl-phenylamino)-quinazolin6-yl]-benzyl}-3-aza-bicyclo[3.1.0]hex6-yl)-methanol;

[3-(4-{4-[1-(4-Methyl-benzyl)-1H-indazol-5-ylamino]-quinazolin-6-yl}-benzyl)-3-aza-bicyclo[3.1.0]hex6-yl]-methanol;

[3-(4-{4-[1-(4-Methoxy-benzyl)-1H-indazol-5-ylamino]-quinazolin-6-yl}-benzyl)-3-aza-bicyclo[3.1.0]hex6-yl]-methanol;

[3-(4-{4-[1-(3-Methyl-benzyl)-1H-indazol-5-ylamino]-quinazolin6-yl}-benzyl)-3-aza-bicyclo[3.1.0]hex6-yl]-methanol;

[3-(4-{4-[1-(3-Methoxy-benzyl)-1H-indazol-5-ylamino]-quinazolin-6-yl}-benzyl)-3-aza-bicyclo[3.1.0]hex6-yl]-methanol;

[3-(4-{4-[1-(2-Fluoro-benzyl)-1H-indazol-5-ylamino]-quinazolin-6-yl}-benzyl)-3-aza-bicyclo[3.1.0]hex-6-yl]-methanol;

(3-{4-[4-(3-Methoxy-4-phenoxy-phenylamino)-quinazolin-6-yl]-benzyl}-3-aza-bicyclo[3.1.0]hex-6-yl)-methanol;

{6-[4-(6-Dimethylamino-3-aza-bicyclo[3.10]hex-3-ylmethyl)-phenyl]-quinazolin-4-yl}-3-methoxy-4-phenoxy-phenyl)-amine;

{6-[4-(6-Dimethylamino-3-aza-bicyclo[3.1.0]hex-3-ylmethyl)-phenyl]-quinazolin-4-yl}-(3-methyl4-phenoxy-phenyl)-amine;

(3-{3-[4-(3-Methyl4-phenoxy-phenylamino)-quinazolin-yl]-benzyl}-3-aza-bicyclo[3.1.0]hex-6-yl)-methanol;

(3-{3-[4-(3-Methoxy4-phenoxy-phenylamino)-quinazolin-6-yl]-benzyl}-3-aza-bicyclo[3.1.0]hex-6-yl)-methanol;

{6-[3-(6-Dimethylamino-3-aza-bicyclo[3.1.0]hex-3-ylmethyl)-phenyl]-quinazolin4-yl}-(3-methoxy4-phenoxy-phenyl)-amine;

{6-[3-(6-Dimethylamino-3-aza-bicyclo[3.1.0]hex-3-ylmethyl)-phenyl]-quinazolin4-yl}-(3-methyl-4-phenoxy-phenyl)-amine;

{6-[3-(6-Amino-3-aza-bicyclo[3.1.0]hex-3-ylmethyl)-phenyl]-quinazolin-4-yl}-(3-methoxy-4-phenoxy-phenyl)-amine;

(3-{4-[4-(3-Methyl4-o-tolyloxy-phenylamino)-quinazolin-6-yl]-benzyl}-3-aza-bicyclo[3.1 0.]hex6-yl)-methanol;

[3-(4-{4-[4-(2-Methoxy-phenoxy)-3-methyl-phenylamino]-quinazolin6-yl}benzyl)-3-aza-bicyclo[3.1.0]hex-6-yl]-methanol; and,

[3-(4-{4-[4-(2-Fluoro-phenoxy)-3-methyl-phenylamino]-quinazolin-6-yl}-benzyl)-3-aza-bicyclo[3.1.0]hex-6-yl]-methanol.

What is claimed is:
1. A compound of the formula 1

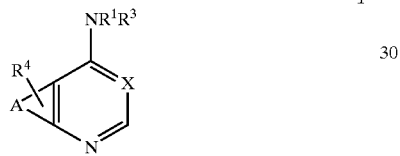

1 or a pharmaceutically acceptable salt or solvate thereof, wherein:
X is N;
A represents a fused 6-membered ring, the fused ring containing a total of 3 double bonds inclusive of the bond in the pyrimidine ring to which it is fused and wherein the carbon atoms of the A moiety are optionally substituted by 1 to 3 $R^5$ groups;
each $R^1$ and $R^2$ is independently H or $C_1$–$C_6$ alkyl;
$R^3$ is —$(CR^1R^2)_m$-$R^8$ wherein m is 0 or 1;
or $R^1$ and $R^3$ are taken together to form a group of the formula

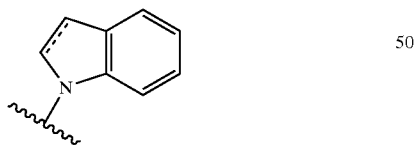

wherein said group is optionally substituted with 1 to 3 $R^5$ groups;
$R^4$ is —$(CR^1R^2)_t(C_6$–$C_{10}$ aryl) or —$(CR^1R^2)_t$(4–10 membered heterocyclic), wherein t is an integer from 0 to 5, wherein said $R^4$ groups are substituted with 1 to 3 groups independently selected from —$(CR^1R^2)_q NR^1R^9$, —$(CR^1R^2)_q NR^9(C_1$–$C_6$ alkanoyl), —$(CR^1R^2)_q O(CR^1R^2)_r R^9$, and —$(CR^1R^2)_q R^9$ wherein q and r are each independently an integer from 0 to 5, and wherein the heterocyclic, aryl and alkyl moieties of the foregoing groups are optionally substituted with 1 to 3 $R^{10}$ groups;

each $R^5$ is independently selected from halo, hydroxy, —$NR^1R^2$, $C_1$–$C_6$ alkyl, trifluoromethyl, $C_1$–$C_6$ alkoxy, and trifluoromethoxy;

each $R^6$ and $R^7$ is independently selected from H, $C_1$–$C_6$ alkyl, —$(CR^1R^2)_t(C_6$–$C_{10}$ aryl), and —$(CR^1R^2)_t$(4–10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing $R^6$ and $R^7$ groups are optionally substituted with 1 to 3 substituents independently selected from halo, cyano, nitro, —$NR^1R^2$, trifluoromethyl, trifluoromethoxy, $C_1$–$C_6$ alkyl, $C_2$–$C_6$ alkenyl, $C_2$–$C_6$ alkynyl, hydroxy, and $C_1$–$C_6$ alkoxy;

each $R^8$ is independently selected from —$(CR^1R^2)_t(C_6$–$C_1$ aryl) and —$(CR^1R^2)_t$(4–10 membered heterocyclic), wherein t is an integer from 0 to 5, 1 or 2 ring carbon atoms of the heterocyclic group are optionally substituted with an oxo (=O) moiety, and each of the foregoing $R^8$ groups is optionally substituted with 1 to 5 $R^{10}$ groups;

$R^9$ is a fused or bridged bicyclic ring or a spirocyclic ring, wherein said ring contains from 5 to 12 carbon atoms in which up to 2 carbon atoms are optionally replaced with a hetero moiety selected from O, $S(O)_j$ wherein j is an integer from 0 to 2, and —$NR^{11}$—, provided that two O atoms, two $S(O)_j$ moieties, an O atom and a $S(O)_j$ moiety, an N atom and an S atom, or an N atom and an O atom are not attached directly to each other, and wherein said ring is saturated or partially unsaturated with up to two carbon-carbon double bonds, and the carbon atoms of said ring are optionally substituted with 1 to 4 $R^{10}$ groups;

or where $R^9$ is as —$NR^1R^9$ then $R^9$ optionally can be taken together with $R^1$ and the nitrogen to which $R^1$ and $R^9$ are attached to form a fused or bridged bicyclic ring or a spirocyclic ring, wherein said ring is saturated and contains from 5 to 12 carbon atoms in which up to 2 carbon atoms are optionally replaced with a hetero moiety selected from O, $S(O)_j$ wherein j is an integer from 0 to 2, and —$NR^1$—, provided that two O atoms, two $S(O)_j$ moieties, or an O atom and a $S(O)_j$ moiety are not attached directly to each other, and wherein the carbon atoms of said rings are optionally substituted with 1 to 4 $R^{10}$ groups;

each $R^{10}$ is independently selected from halo, cyano, nitro, trifluoromethoxy, trifluoromethyl, azido, hydroxy, $C_1$–$C_6$ alkoxy, $C_1$–$C_{10}$ alkyl, $C_2$–$C_6$ alkenyl, $C_2$–$C_6$ alkynyl, —$C(O)R^5$, —$C(O)OR^6$, —$OC(O)R^6$, —$NR^6C(O)R^7$, —$C(O)NR^6R^7$, —$NR^6R^7$, —$NR^6OR^7$, —$SO_2NR^6R^7$, —$S(O)_j$ ($C_1$–$C_6$ alkyl) wherein j is an integer from 0 to 2, —$(CR^1R^2)_t(C_6$–$C_{10}$ aryl), —$(CR^1R^2)_t$(4–10 membered heterocyclic), —$(CR^1R^2)_q C(O)(CR^1R^2)_t (C_6$–$C_{10}$ aryl), —$(CR^1R^2)_q C(O)(CR^1R^2)_t$(4–10 membered heterocyclic), —$(CR^1R^2)_t O(CR^1R^2)_q (C_6$–$C_{10}$ aryl), —$(CR^1R^2)_t O(CR^1R^2)_q$(4–10 membered heterocyclic), —$(CR^1R^2)_q SO_2(CR^1R^2)_t (C_6$–$C_{10}$ aryl), and —$(CR^1R^2)_q SO_2(CR^1R^2)_t$(4–10 membered heterocyclic), wherein q and t are each independently an integer from 0 to 5, 1 or 2 ring carbon atoms of the heterocyclic moieties of the foregoing $R^{10}$ groups are optionally substituted with an oxo (=O) moiety, and the alkyl, alkenyl, alkynyl, aryl and heterocyclic moieties of the foregoing $R^{10}$ groups are optionally substituted with 1 to 3 substituents independently selected from halo, cyano, nitro, trifluoromethyl, trifluoromethoxy, azido, —OR$^6$, —C(O)R$^6$, —C(O)OR$^6$, —OC(O)R$^6$, —NR$^6$C(O)R$^7$, —C(O)NR$^6$R$^7$, —NR$^6$R$^7$, —NR$^6$OR$^7$, C$_1$–C$_6$ alkyl, C$_2$–C$_6$ alkenyl, C$_2$–C$_6$ alkynyl, —(CR$^1$R$^2$)$_t$(C$_6$–C$_{10}$ aryl), and —(CR$^1$R$^2$)$_t$(4–10 membered heterocyclic), wherein t is an integer from 0 to 5;

R$^{11}$ is H, C$_1$–C$_6$ alkyl, —C(O)R$^6$ or —SO$_2$R$^6$;

and wherein any of the above-mentioned substituents comprising a CH$_3$ (methyl), CH$_2$ (methylene), or CH (methine) group which is not attached to a halogeno, SO or SO$_2$ group or to a N, O or S atom optionally bears on said group a substituent selected from hydroxy, halo, C$_1$–C$_4$ alkyl, C$_1$–C$_4$ alkoxy and —NR$^1$R$^2$.

2. A compound according to claim 1 wherein R$^4$ is —(CR$^1$R$^2$)$_t$(C$_6$–C$_{10}$ aryl) or —(CR$^1$R$^2$)$_t$(4–10 membered heterocyclic), wherein t is an integer from 0 to 5, wherein said R$^4$ groups are substituted with 1 to 3 groups independently selected from —(CR$^1$R$^2$)$_q$NR$^1$R$^9$, —(CR$^1$R$^2$)$_q$NR$^9$(C$_1$–C$_6$ alkanoyl), —(CR$^1$R$^2$)$_q$O(CR$^1$R$^2$)$_r$R$^9$, and —(CR$^1$R$^2$)$_q$R$^9$ wherein q and r are each independently an integer from 0 to 3, and wherein the heterocyclic, aryl and alkyl moieties of the foregoing groups are optionally substituted with 1 to 3 R$^{10}$ groups.

3. A compound according to claim 1 wherein R$^3$ is —(CR$^1$R$^2$)$_m$—R$^8$ wherein m is 0 or 1 and R$^8$ is selected from —(CR$^{R2}$)$_t$(phenyl), —(CR$^1$R$^2$)$_t$(pyridyl), —(CR$^1$R$^2$)$_t$(pyrimidinyl), —(CR$^1$R$^2$)$_t$(indolyl), —(CR$^1$R$^2$)$_t$(indazolyl) and —(CR$^1$R$^2$)$_t$(benzimidazolyl), wherein t is an integer from 0 to 5, and each of the foregoing R$^8$ groups is optionally substituted with 1 to 5 R$^{10}$ groups.

4. A compound according to claim 1 selected from the group consisting of:
{6-[4-(6-Amino-3-aza-bicyclo[3.1.0]hex-3-ylmethyl)-phenyl]-quinazolin-4-yl}-(4-phenoxy-phenyl)-amine;
(3-{4-[4-(4-Benzyl-phenylamino)-quinazolin-6-yl]-benzyl}-3-aza-bicyclo[3.1.0]hex-6-yl)-methanol:
(3-{4-[4-(4-Phenoxy-phenylamino)-quinazolin-6-yl]-benzyl}-3-aza-bicyclo[3.1.0]hex-6-yl)-methanol;
(3-{4-[4-(1-Benzenesulfonyl-1H-indol-5-ylamino)-quinazolin-6-yl]-benzyl}-3-aza-bicyclo[3.1.0]hex-6-yl)-methanol;
(6-{4-[(1-Aza-bicyclo[2.2.2]oct-3-ylamino)-methyl]-phenyl}-quinazolin-4-yl)-(4-phenoxy-phenyl)-amine;
(6-{4-[(1-Aza-bicyclo[2.2.2]oct-3-ylamino)-methyl]-phenyl}-quinazolin-4-yl)-(4-benzyl-phenyl)-amine;
6-{4-[(1-Aza-bicyclo[2.2.2]oct-3-ylamino)-methyl]-phenyl}-quinazolin-4-yl)-(1-benzenesulfonyl-1H-indol-5-yl)-amine;
6-{4-[(3-Aza-bicyclo[3.1.0]hex-6-ylamino)-methyl]-phenyl}-quinazolin-4-yl)-(4-phenoxy-phenoxy)-amine;
3-{4-[4-(4-Benzyl-phenylamino)-quinazolin-6-yl]-benzylamino}8-methyl-8-aza-bicyclo[3.2.1]octan6-ol;
(4-Benzyl-phenyl)-{6-[4-(6-methoxymethyl-3-aza-bicyclo[3.1.0]hex-3-ylmethyl)-phenyl]-quinazolin4-yl}amine
{6-[4-(6-Methoxymethyl-3-aza-bicyclo[3.1.0]hex-3-ylmethyl)-phenyl]-quinazolin-4-yl}-(4-phenoxy-phenyl)-amine;
(3-{4-[4-(4-[1,2,3]Thiadiazol-5-yl-phenylamino)-quinazolin-6-yl]-benzyl}-3-aza-bicyclo[3.1.0]hex-6-yl)-methanol;
(3-{4-[4-(4-Cyclohexyl-phenylamino)-quinazolin-6-yl]-benzyl}-3-aza-bicyclo[3.1.0]hex-6-yl)-methanol;
(3-{4-[4-(4-p-Tosyloxy-phenylamino)-quinazolin6-yl]-benzyl}-3-aza-bicyclo[3.1.0]hex6-yl)-methanol;
(3-{4-[4-(Biphenyl-4-ylamino)-quinazolin-6-yl]-benzyl}-3-aza-bicyclo[3.1.0]hex6-yl)-methanol;
(3-{4-[4-(4-Ethyl-phenylamino)-quinazolin-6-yl]-benzyl}-3-aza-bicyclo[3.1.0]hex-6-yl)-methanol;
4-{6-[4-(6-Hydroxymethyl-3-aza-bicyclo[3.1.0]hex-3-ylmethyl)-phenyl]-quinazolin-4-ylamino}-N-phenyl-benzamide;
[3-(4-{4-[1-(Propane-2-sulfonyl)-1H-indol-5-ylamino]-quinazolin-6-yl}-benzyl)-3-aza-bicyclo[3.1.0]hex-6-yl]-methanol;
(3-{4-[4-(1-Benzyl-1H-indazol-5-ylamino)-quinazolin-6-yl]-benzyl}-3-aza-bicyclo[3.1.0]hex-6-yl)-methanol;
(1-Benzenesulfonyl-1H-indol-5-yl)-(6-{4-[(3-oxa-bicyclo[3.1.0]hex-6-ylamino)-methyl]-phenyl}-quinazolin-4-yl)-amine;
8-{4-[4-(1-Benzenesulfonyl-1H-indol-5-ylamino)-quinazolin6-yl]-benzyl}-8-aza-bicyclo[3.2.1]octan-3-ol;
8-(4-{4-[1-( Propane-2-sulfonyl)-1H-indol-5-ylamino]-quinazolin-6-yl}-benzyl)-8-aza-bicyclo[3.2.1]octan-3-ol;
8-{4-[4-(4-Phenoxy-phenylamino)-quinazolin6-yl]-benzyl}-8-aza-bicyclo[3.2.1]octan-3-ol;
8-{4-[4-(1-Benzyl-1H-indol-5-ylamino)-quinazolin6-yl]-benzyl}-8-aza-bicyclo[3.2.1]octan-3-ol;
(3-{4-[4-(6-Phenoxy-pyridin-3-ylamino)-quinazolin-6-yl]-benzyl}-3-aza-bicyclo[3.1.0]hex-6-yl)-methanol;
(3-{5-[4-(4-Benzyl-phenylamino)-quinazolin6-yl]-pyridin-2-ylmethyl}-3-aza-bicyclo[3.1.0]hex-6-yl)-methanol;
{3-[4-(4-Phenoxy-phenylamino)-quinazolin-6ylmethyl]-3-aza-bicyclo[3.1.0]hex-6-yl}methanol;
(5-{4-[4-(1-Benzenesulfonyl-1H-indol-5-ylamino)-quinazolin-6-yl]-benzyl)}-5-aza-spiro[2.5]oct-1-yl)-methanol;
(5-{4-[4-(4-Phenoxy-phenylamino)-quinazolin-6-yl]-benzyl}-5-aza-spiro[2.5]oct-1-yl)-methanol; (6-{4-[4-(1-Benzenesulfonyl-1H-indol-5-ylamino)-quinazolin-6-yl]-benzyl}-aza-spiro[2.5]oct-1-yl)-methanol;
(6-{4-[4-(4-Phenoxy-phenylamino)-quinazolin6-yl]-benzyl}-6aza-spiro[2.5]oct-1-yl)-methanol;
(5-{4-[4-(1-Benzenesulfonyl-1H-indol-5-ylamino)-quinazolin6-yl]-benzyl}-5-aza-spiro[2.4]hept-1-yl)-methanol;
(5-{4-[4-(4-Phenoxy-phenylamino)-quinazolin6-yl]-benzyl}-5-aza-spiro[2.4]hept-1-yl)-methanol;
(5-{4-[4-(4-Phenoxy-phenylamino)-quinazolin6-yl]-benzyl}-5-aza-spiro[2.5]oct-1-yl)-methanol; and the pharmaceutically acceptable salts and solvates of the foregoing compounds.

5. A method of preparing a compound of claim 1 which comprises either (a) reacting a compound of the formula 5 with a compound of the formula 6

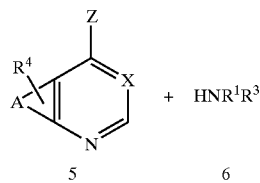

+ HNR$^1$R$^3$ 5      6 wherein Z is a leaving group and A, X, R$^1$, R$^3$, and R$^4$ are as defined in claim 1, or (b) reacting a compound of the formula 2 with a compound of the formula 6

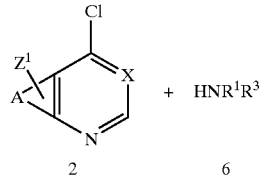

+ HNR$^1$R$^3$ 2      6 wherein X, A, R$^1$, and R$^3$ are as defined in claim 1 and Z$^1$ is an activating group, to provide an intermediate of the formula 7

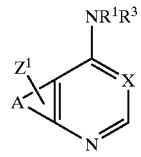

7 wherein Z$^1$, X, A, R$^1$, and R$^3$ are as defined in claim 1, and treating the compound of formula 7 with a coupling partner of the formula X$^1$—(CR$^1$R$^2$)$_t$(C$_6$–C$_{10}$ aryl) or X$^1$—(CR$^1$R$^2$)$_t$(4–10 membered heterocyclic), wherein t, R$^1$ and R$^2$ are as defined in claim 1 as provided in the definition of R$^4$, the aryl and heterocyclic groups of the foregoing groups are substituted with a group that includes an aldehyde or acid moiety, and X$^1$ is —B(OH)$_2$ or —Sn(C$_1$–C$_5$ alkyl)$_3$, to provide a compound of formula 8

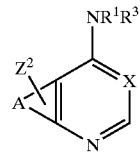

8 wherein X, A, R$^1$, and R$^3$ are as defined above, and Z$^2$ is —(CR$^1$R$^2$)$_t$(C$_6$–C$_{10}$ aryl) or —(CR$^1$R$^2$)$_t$ (4–10 membered heterocyclic), wherein t, R$^1$ and R$^2$ are as defined in claim 1, and the aryl and heterocyclic groups of the foregoing Z$^2$ groups are substituted with a group that includes an aldehyde or acid moiety, and modifying said aldehyde or acid moiety to introduce a group selected from —(CR$^1$R$^2$)$_q$NR$^1$R$^9$, —(CR$^1$R$^2$)$_q$NR$^9$(C$_1$–C$_6$ alkanoyl), —(CR$^1$R$^2$)$_q$OR$^9$ and —(CR$^1$R$^2$)$_q$R$^9$ wherein R$^1$, R$^2$, R$^9$ and q are as defined in the definition of R$^4$ in claim 1.

6. A pharmaceutical composition for the treatment of skin cancer in a mammal comprising an amount of a compound of claim 1 that is effective in treating skin cancer, and a pharmaceutically acceptable carrier.

7. A method for the treatment of skin cancer in a mammal which comprises administering to said mammal an amount of a compound of claim 1 that is effective in treating skin cancer in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

8. A method for the treatment of skin cancer in a mammal comprising administering to said mammal an amount of a compound of claim 1 that is effective in treating skin cancer.

* * * * *